(12) United States Patent
Herrnsdorf

(10) Patent No.: US 10,376,228 B2
(45) Date of Patent: Aug. 13, 2019

(54) X-RAY DETECTION DEVICE

(71) Applicant: RTI Group AB, Moelndal (SE)

(72) Inventor: Lars Herrnsdorf, Lindome (SE)

(73) Assignee: RTI Group AB, Moelndal (SE)

( * ) Notice: Subject to any disclaimer, the term of this patent is extended or adjusted under 35 U.S.C. 154(b) by 8 days.

(21) Appl. No.: 15/845,618

(22) Filed: Dec. 18, 2017

(65) Prior Publication Data
US 2019/0183441 A1    Jun. 20, 2019

(51) Int. Cl.
*A61B 6/00* (2006.01)
*G21K 1/10* (2006.01)
*A61B 6/03* (2006.01)

(52) U.S. Cl.
CPC ............ *A61B 6/4208* (2013.01); *A61B 6/032* (2013.01); *A61B 6/4085* (2013.01); *G21K 1/10* (2013.01)

(58) Field of Classification Search
CPC ..... A61B 6/4208; A61B 6/032; A61B 6/4085; G21K 1/10
See application file for complete search history.

(56) References Cited

U.S. PATENT DOCUMENTS

| | | | | |
|---|---|---|---|---|
| 4,757,201 A | * | 7/1988 | Kanter | A23L 3/263 250/337 |
| 5,081,362 A | * | 1/1992 | Vargo | G01T 7/00 250/472.1 |

(Continued)

FOREIGN PATENT DOCUMENTS

| CA | 2297088 A1 | 12/1999 |
|---|---|---|
| PA | S614987 A | 1/1986 |
| WO | WO 2010/140944 A1 | 12/2010 |

OTHER PUBLICATIONS

Herrnsdorf, L., et al., "Point dose profile measurements using solid-state detectors in characterization of Computed Tomography systems", *Nuclear Instruments and and Methods in Physics Research Section A: Accelerators, Spectrometers, Detectors and Associated Equipment*, Aug. 2009, pp. 223-225, vol. 607, issue 1, Elsevier, B.V., Netherlands.
International Searching Authority, International Search Report and Written Opinion, for International Application No. PCT/EP2018/084921, dated May 10, 2019, 19 pages, European Patent Office, Europe.

*Primary Examiner* — Christine S. Kim
(74) *Attorney, Agent, or Firm* — Alston & Bird LLP

(57) ABSTRACT

The invention concerns an X-ray detection device comprising an X-ray sensing member and an X-ray energy filter comprising an attenuation member configured to attenuate low-energy X-rays to a greater extent than high-energy X-rays in a beam or field of X-radiation directed towards the X-ray sensing member. The invention is characterized in that the attenuation member is arranged to extend in a spatial manner at least partly around the X-ray sensing member so as to subtend at least a working solid angle in relation to the X-ray sensing member, wherein the attenuation member, at least over a working area corresponding to the working solid angle, is provided with a plurality of low-attenuation zones distributed over the working area of the attenuation member, wherein the low-attenuation zones are configured to attenuate X-rays only to a small or negligible extent so as to allow passage of both low-energy and high-energy X-rays to a substantially similar extent through the attenuation member towards the X-ray sensing member, wherein the low-attenuation zones are distributed in relation to the X-ray sensing member in such a way that, when the X-ray detection device is exposed to a beam or field of parallel X-radiation that is directed towards the X-ray sensing member within the working solid angle and that has a width that covers a projected area of the energy filter, only a first portion of a total surface of the X-ray sensing member facing the beam (Continued)

or field of X-radiation is directly exposed to low-attenuated X-rays that pass through the low-attenuation zones, whereas a second remaining portion of the total surface of the X-ray sensing member facing the beam or field of X-radiation is directly exposed only to X-rays that pass through the attenuation member, wherein the relation between i) the first portion of the total surface of the X-ray sensing member facing the beam or field of X-radiation and ii) said total surface of the X-ray sensing member facing the beam or field of X-radiation, is substantially constant irrespective of a spatial angle of incidence of the beam or field of X-radiation that falls within the working solid angle.

37 Claims, 9 Drawing Sheets

(56) References Cited

U.S. PATENT DOCUMENTS

| | | | | |
|---|---|---|---|---|
| 8,829,453 | B2 * | 9/2014 | Bengtsson | G01T 1/026 250/370.09 |
| 2001/0052572 | A1 * | 12/2001 | Mikami | G01T 1/00 250/394 |
| 2012/0112099 | A1 * | 5/2012 | Coleman | G01T 1/08 250/473.1 |
| 2017/0112462 | A1 * | 4/2017 | O'Hare | A61B 6/032 |
| 2018/0339174 | A1 * | 11/2018 | Kilby | A61N 5/1043 |
| 2019/0060673 | A1 * | 2/2019 | McKenna | A61N 5/1075 |

* cited by examiner

X-RAY DETECTION DEVICE

BACKGROUND

Related Field

This invention relates to an X-ray detection device comprising an X-ray sensing member and an X-ray energy filter comprising an attenuation member configured to attenuate low-energy X-rays to a greater extent than high-energy X-rays in a beam or field of X-radiation directed towards the X-ray sensing member. In particular, the invention relates to a detection device that exhibits a reduced X-ray energy dependency.

Description of Related Art

Of all the artificial X-ray sources, medical radiation sources supply the largest dose to the human population, and of these, Computed Tomography (CT) contributes to 70% of the total dose. A CT examination gives 10-50 times more dose to a patient than corresponding conventional examinations, and therefore quality control is important and should be made regularly.

The absorbed dose to a patient is the result of both primary radiation and scattered radiation from the surrounding tissue. For quality assurance, measurements of the dose from CT are performed in a phantom in order to include internal scattered radiation within the body. Dose measurements are traditionally done with a 100-mm-long, pencil-shaped ionization chamber. However, at present a CT with beam collimation of up to 160 mm is available, which results in an incomplete measurement of the primary radiation using the standard ion chamber. Measuring the dose profile can be done using thermo-luminescent dosimeters (TLD), optically stimulated luminescence (OSL), or X-ray film. Drawbacks of these methods are that they are either expensive, time consuming or obsolete.

Recently, it has been proposed the use of a semiconductor detector diode for point dose measurement. Semiconductor X-ray detectors/sensors are as such well known and generally comprise a relatively flat detecting portion with back and front electrode contacts arranged on opposite sides of the detecting portion. The semiconductor detector proposed is made of Si and arranged in a PMMA (poly methyl methacrylate) rod that in turn is arranged in an aluminium (i.e., aluminum) cylinder. This type of detection device has e.g. the potential of having a much higher sensitivity than a small ion chamber.

Commercially available solid-state detectors for point dose measurements are typically mounted in a package with a high Z material acting as the back contact causing unsymmetrical response, which is a major drawback in a CT dose profile application. As described by Herrnsdorf et al. (L. Herrnsdorf et al., Nucl. Instr. and Meth. A (2009), doi: 10.1016/j.nima.2009.03.159), substituting this high Z back contact with aluminum back and front contacts, and mounting the detector diode in parallel to the incoming radiation, improved the device considerably with regard to dose and dose profile measurements.

WO2010/140944 discloses a further improved detection device where the first and second electrodes of the X-ray sensing member are arranged on the same side of the sensing member so as to avoid that any of the electrical conductors, typically gold wires, has to be positioned in the radiation field outside of the sensing member. Further, to reduce the angular dependency of the device (in the z-direction) an annular cavity is arranged around the sensing member in a surrounding tissue equivalent material (PMMA).

Although the device of WO2010/140944 may function properly in its intended application there is a need for improvements in the field of X-ray detection devices; not only with regard to detector response, such as improved symmetry and reduced angular and energy dependency (in all directions), but also to the manufacturing process. Improvements are needed not only in CT dose measurements as discussed above but also in other applications.

BRIEF SUMMARY

The invention concerns an X-ray detection device, comprising an X-ray sensing member and an energy filter comprising an attenuation member configured to attenuate low-energy X-rays to a greater extent than high-energy X-rays in a beam or field of X-radiation directed towards the X-ray sensing member.

The invention is characterized in that the attenuation member is arranged to extend in a spatial manner at least partly around the X-ray sensing member so as to subtend at least a working solid angle in relation to the X-ray sensing member, wherein the attenuation member, at least over a working area corresponding to the working solid angle, is provided with a plurality of low-attenuation zones distributed over the working area of the attenuation member, wherein the low-attenuation zones are configured to attenuate X-rays only to a small or negligible extent so as to allow passage of both low-energy and high-energy X-rays to a substantially similar extent through the attenuation member towards the X-ray sensing member, wherein the low-attenuation zones are distributed in relation to the X-ray sensing member in such a way that, when the X-ray detection device is exposed to a beam or field of parallel X-radiation that is directed towards the X-ray sensing member within the working solid angle and that has a width that covers a projected area of the energy filter, only a first portion of a total surface of the X-ray sensing member facing the beam or field of X-radiation is directly exposed to low-attenuated X-rays that pass through the low-attenuation zones, whereas a second remaining portion of the total surface of the X-ray sensing member facing the beam or field of X-radiation is directly exposed only to X-rays that pass through the attenuation member, wherein the relation between i) the first portion of the total surface of the X-ray sensing member facing the beam or field of X-radiation and ii) said total surface of the X-ray sensing member facing the beam or field of X-radiation, is substantially constant irrespective of a spatial angle of incidence of the beam or field of X-radiation that falls within the working solid angle.

A well-known physical effect that forms a basis in the use of X-ray sensing members and energy filters is that high-energy X-rays generally pass through materials to a higher extent than low-energy X-rays irrespective of any exact definition of what is a "low" or a "high" energy range (if disregarding some resonance energy phenomena). This means for instance that the relative response sensitivity of a regular thin semiconducting X-ray sensing member, such as a silicon sensor, is much higher for low-energy X-rays, such as in the range 10-30 keV, than for high-energy X-rays, such as in the range 100-150 keV. It also means that an energy filter made of e.g. steel or other material generally attenuates (blocks) low-energy X-rays to a higher extent than high-energy X-rays.

The above definition of the inventive device means that the device is structured in such a way that when the device is exposed to a beam or field of X-radiation of the type described above directed towards the sensing member in any angle of incidence within the working solid angle, the attenuation member "shades" the second portion of the total surface of the X-ray sensing member facing the beam or field of X-radiation so that only a first, defined and substantially constant portion of the sensing member surface (facing the beam or field of X-radiation) is directly exposed to low-attenuated X-rays that pass through the low-attenuation zones. Since low-energy X-rays are attenuated (damped, blocked) by the attenuation member to a larger extent than high-energy X-rays, the exposed area of the sensing member, i.e. the effective sensing area, will be smaller for low-energy X-rays (which can only pass through the low-attenuation zones and hit the first portion of the total surface area facing in the relevant direction) than for high-energy X-rays (which can pass through both the attenuation member and the low-attenuation zones and hit both the first and the second surface portions, i.e. the entire surface area facing in the relevant direction). This evens out the sensing member's energy response curve. And because the relation between the first portion of the sensing member surface area (facing in the relevant direction) and the total sensing member surface (facing in the relevant direction) does not change within the working solid angle, the sensing member's energy response curve is consistent within the working solid angle.

A main effect of such a structure is that the response sensitivity of the detection device can be made less dependent on the X-ray energy, even more or less independent of the X-ray energy, by letting the device work within the working solid angle.

To be able to measure dose correctly it is important to have a low energy and angle dependency (within the working solid angle). This is of particular importance when the X-ray filtration and/or the X-radiation generator kV used is not known and the radiation is penetrated from different angles during an exposure (e.g. CT, CBCT and tomosynthesis). There are also IEC standards that set limits for the energy and angular dependency (IEC 61674 IEC 61674: 2012 Standard|Medical electrical equipment—Dosimeters with ionization chambers and/or semiconductor detectors as used in X-ray diagnostic imaging). As described further below, the detection device of the present disclosure can be arranged to exhibit also a low angle dependency.

In practice a beam or field of X-ray radiation will have a width that is much larger than the projected area of the energy filter, i.e. the width of the filter as seen from the radiation, since the filter will typically be less than 10 mm across which is "small" in relation to a typical X-radiation field.

The choice of size, number and exact distribution of the low-attenuation zones as well as the choice of material, thickness etc. of the attenuation member, depends on the type, shape and size of the sensing member, shape and dimension of the energy filter, distance between sensing member and attenuation member, the type of application (e.g. the X-ray energy spectrum to be used), etc. For instance, for a spherical attenuation member surrounding a flat sensing member, the low-attenuation zones might be allowed to be larger in areas facing a flat side of the sensing member than in areas facing an edge of the sensing member. The reason for this is that a certain exposed surface area part on the sensing member that a certain individual low-attenuation zone exposes may constitute a too great portion of the total surface exposed on an edge of the sensing member (for geometrical reasons, a certain low-attenuation zone may expose, say, 10% of a flat side of detector if positioned right above the flat side but, say, 30% of the entire edge surface if positioned right above the edge of the sensing member). In any case, a particular portion of the X-radiation directed towards the sensing member within the working solid angle (i.e. a portion corresponding to the first portion of the exposed sensing member surface) should be allowed to pass through the plurality of low-attenuation zones as described above.

As mentioned above, the exact design of the energy filter depends on a number of factors (size and number of low-attenuation zones; shape of sensing member; X-ray energy spectrum to be used; etc.). Therefore, the distribution of the low-attenuation zones in relation to the X-ray sensing member, which is a feature relating to the physical structure of the energy filter, has been defined with reference to an imaginary beam or field of X-radiation that has certain properties. Besides that these properties are fulfilled for most X-radiation fields used in practice, these properties are selected to clarify the definition of the physical structure of the energy filter. For instance, a very narrow X-ray beam, i.e. a beam that has a width that does not cover a projected area of the energy filter, may pass through only one single low-attenuation zone and hit the sensing member surface in one small spot. Such X-rays beams are excluded from the imaginary beam or field of X-radiation used to define the distribution of the low-attenuation zones in relation to the X-ray sensing member. The definition of the detection device relates only to structural features; whether the device actually is exposed to any beam or field of X-radiation is not relevant for the definition.

Which relation to choose between the first portion of the total directly exposed sensing member surface and this total surface depends mainly on the energy spectrum of the X-radiation to be used. The first portion may constitute 5-80% of the total sensing member surface that is directly exposed to incoming low- and high-energy X-radiation (i.e. the total target surface facing the beam or field of X-radiation). In a typical example, the first portion constitutes around 25% of the total surface of the X-ray sensing member facing the beam or field of X-radiation. Preferably, this relation is 10-50%, preferably 15-35%, and more preferably 20-30%. It should be noted that the term "total surface" refers in this context to the sensing member surface that faces the beam or field of radiation and form a target surface for the radiation. It does not include sensing member surfaces that are "hidden" behind other sensing member surfaces that face the beam or field of X-radiation, such as a backside or hidden sides and edges of the sensing member. For instance, for a flat sensing member the total sensing member target surface is much smaller if the X-radiation is directed towards an edge of the sensing member, i.e. in parallel with the flat sides, than if the X-radiation is directed perpendicularly towards one of the flat sides. (The sensing member sensitivity in the two directions may however be similar since the decrease in sensing member target surface may be cancelled out by an increase in sensing member depth, which increases the fraction of X-ray photons that interact with the sensing member during the passage through the sensing member.)

In an embodiment of the invention the working solid angle is at least 10°, or at least 20°, or at least 45°, or at least 90°, or at least 180° (hemisphere), or at least 270°, or 360° (entire sphere). For angles less than 180° the solid angle can, for visualization and easier understanding, be regarded to be a cone having an apex angle corresponding to the solid angle. For example, a solid angle of 90° may be said to correspond to a cone with its apex located at the X-ray sensing member and having an apex angle of 90°.

A working solid angle of 360° means that the attenuation member and the distribution of low-attenuation zones extend spherically (4π) around the X-ray sensing member (which not necessarily means that the energy filter or the attenuation member must have the shape of the sphere, the shape may instead be polyhedral). With a working solid angle of 360° the detection device has a reduced energy dependence or even a uniform energy dependence in all directions. This is very useful in certain applications, such as when the X-ray filtration and/or the X-radiation generator kV used is not known and the radiation is penetrated from different angles during an exposure (e.g. CT, CBCT and tomosynthesis).

In other applications a smaller working solid angle may be sufficient, such as when the X-ray beam is directed from above as in conventional X-ray imaging situations. A working solid angle of at least 10° (i.e. ±5° from a reference angle) corresponds to limits stated in IEC standards (IEC 61674 IEC 61674:2012 Standard|Medical electrical equipment—Dosimeters with ionization chambers and/or semiconductor detectors as used in X-ray diagnostic imaging).

In case the working solid angle is (close to) 360° the attenuation member preferably comprises (at least) two parts that are connectable to each other so that the sensing member more easily can be introduced inside and taken out from the attenuation member.

In an embodiment of the invention the attenuation member comprises one or several elements having an atomic number (Z) of at least 23 and wherein the one or several elements constitutes at least 50% of the weight of the attenuation member, at least within the working solid angle. A reasonably high amount and density of an element having a reasonably high Z is needed for a useful attenuation effect. It is well known that too much of an element having a very high Z would block too much of the X-radiation. Preferably, the attenuation member is made of stainless steel. This material comprises a lot of iron which is useful as attenuator, and stainless is suitable for additive manufacturing (3D printing) of the attenuation member/energy filter. The attenuation member may alternatively be made of e.g. brass, copper or iron.

In an embodiment of the invention the attenuation member has a convex side and a concave side, wherein the concave side is directed towards the X-ray sensing member. Preferably, the attenuation member has the general shape of a sphere, or a part of a sphere, and/or the general shape of a polyhedral, or a part of a polyhedral. Such a shape can be made by additive manufacturing. A polyhedral shape may alternatively be made by repeated folding of a flat material.

In an embodiment of the invention the attenuation member, at least within the working solid angle, has a thickness in the range 0.3-3 mm, preferably 0.5-2 mm. A suitable example is to use stainless steel and a thickness of 1.0 mm.

In an embodiment of the invention the low-attenuation zones exhibit a lower area-specific density than the attenuation member. This can be arranged by providing the attenuation member with a smaller thickness at the low-attenuation zones and/or by using a material at the low-attenuation zones that has a lower density.

In an embodiment of the invention the low-attenuation zones form isolated zones and wherein the attenuation member extends over an area between the low-attenuation zones. Preferably, the attenuation member forms a single component that is homogeneous over the working area of the working solid angle (where the low-attenuation zones form isolated zones). Alternatively, the attenuation member may comprise a plurality of parts that are arranged side by side in e.g. a plastic matrix that extends over the working area.

In an embodiment of the invention the low-attenuation zones form through-holes in the attenuation member. With regard to production it is likely to be easier to provide the attenuation member with open holes, which in practice have zero attenuation, than varying thickness and/or varying materials. A homogeneous attenuation member provided with through-holes can be made by additive manufacturing.

In an embodiment of the invention the X-ray sensing member is arranged onto a supporting arrangement comprising an outer support element, wherein the outer support element and the attenuation member are configured to fit together and be connected to each other so as to define a working position for the X-ray sensing member in relation to the attenuation member. Some kind of supporting arrangement is suitable for handling of the sensing member and by involving an outer support element that connects to the attenuation member it is possible to provide for positioning of the sensing member, e.g. centrally in a spherical attenuation member.

In an embodiment of the invention the outer support element, when connected to the attenuation member, forms part of the attenuation member and wherein the low-attenuation zones are distributed also over the outer support element. This way it is possible to achieve a working solid angle of 360°.

In an embodiment of the invention the supporting arrangement comprises an inner support element that extends between the outer support element and the X-ray sensing member. The inner support element may be made of a material that exhibits a low or negligible attenuating effect on X-rays, such as a plastic material. In a variant, the inner support element and the outer support element forms one integral component, wherein the inner support element has a physical structure adapted to exhibit a low or negligible attenuating effect on X-rays directed towards the sensing member. Typically, this means that the inner support element and the outer support element are made of the same material, such as stainless steel, and that this integral component is produced by additive manufacturing. The physical structure of the inner support element may involve a threadlike structure with a lot of openings, and it may also be adapted to any low-attenuation zones in the outer support element to reduce or eliminate the effect on the measurements. An advantage of using such an integral component this is that it reduces the total number of components.

In an embodiment of the invention the device comprises first and second electric connectors connected to the X-ray sensing member, wherein the outer support element is provided with at least one through-hole and wherein the first and second electric connectors extend through the at least one through-hole in the outer support element.

In an embodiment of the invention the X-ray sensing member has a flat shape with first and second main surfaces facing in opposite directions and a perimeter edge. This is the typical shape of a semiconducting X-ray sensing member, which is very suitable for the detection device.

In an embodiment of the invention the attenuation member is arranged to subtend the working solid angle in relation to the edge of the X-ray sensing member, wherein the working solid angle in relation to the edge is at least 10°, or at least 20°, or at least 45°, or at least 90°, or at least 180° (hemisphere), or at least 270°, or 360° (entire sphere). Alternatively, the working solid angle may be related in a similar way to a normal (at right angles) to one of the main surfaces of the sensing member. Generally, when the working solid angle is 360° the energy filter surrounds the sensing member in all directions. The value 360° should, however, be interpreted as substantially 360°, wherein the energy filter surrounds the sensing member in substantially all directions. A small fraction of the 360° solid angle may in practice form an exception for various reasons.

In an embodiment of the invention the X-ray sensing member is a semiconducting sensing member provided with first and second electrodes arranged at one of the main surfaces of the X-ray sensing member or one electrode at each main surface of the X-ray sensing member, wherein the device comprises first and second electric conductors connected to the first and second electrodes, respectively, wherein the device comprises a non-conducting substrate provided with at least a first conducting track that forms the first electric conductor, and wherein the connection between the first conducting track and the first electrode is arranged by means of an anisotropic conducting compound.

Thus, instead of using gold wires and wire bonding for connecting the wires to the electrodes as disclosed in e.g. WO2010/140944, this embodiment makes use of a conducting track arranged on a non-conducting substrate in combination with an anisotropic conductive compound for providing the connection to the electrodes.

Both the gold wires and their bonds at the electrode surface interact strongly with X-radiation and are clearly seen on X-ray images. Such wires and bonds thus affect the output signal from the X-ray sensing member if positioned in the radiation field and contribute to the angular dependency of the device. This embodiment provides for the possibility to eliminate or at least reduce the angular dependency originating from the conductors and their bonding to the electrodes. This is particularly useful when the working solid angle of the energy filter is 360° or close to 360° since the detection device can be made more or less independent of both energy and direction of the X-radiation. Moreover, this embodiment provides for a simplified and more efficient production method compared to contacting by bonding gold wires.

A non-conducting substrate, such as a flexible plastic substrate, is suitable for carrying thin conductive tracks made of copper (or e.g. aluminum) that interacts with X-rays to a much lesser extent than gold (since the attenuation roughly is proportional to $Z^3$ or even $Z^4$ for diagnostic X-ray beam qualities).

Consequently, using the above contacting concept provides for the possibility to significantly reduce the effect of the conductors compared to a device provided with gold wires. Very thin gold wires might be acceptable with regard to X-ray interaction, but gold wires with a diameter of less than around 50 µm tend to break when used in an application of the type of interest in this disclosure.

Anisotropic conductive compounds are known as such but have not, as far as known to the applicant, been used for connecting the electrodes of X-ray sensing members to conductors, at least not in the type of applications described in the present disclosure. This idea is partly based on the inventor's realization that a certain physical property of such compounds is of particular interest for the applications in question, i.e. the property of being (close to) transparent for X-rays (provided that the compound is not present in very large amounts). In combination with conductive tracks on a non-conducting substrate, this property is of great importance for reducing or eliminating the angular response dependency for an X-ray detection device.

An anisotropic conductive compound comprises conductive particles that are distributed in a non-conducting resin or matrix. The particles may be made of or covered with Ag or other conductive material, and the size of the particles is typically in the range from a few µm up to around 10 µm. The resin may be a thermosetting adhesive (based on e.g. epoxy or acryl) allowing the compound to be used both for conducting electricity and for holding components together. As a starting point, the amount of conductive particles per volume unit of the compound is sufficiently low to create a distance between all or most of the particles and thus to make the compound non-conducting in all directions. By exposing the compound to a pressure between two components, in this case between the first conducting track and the first electrode, the conductive particles are brought into contact and the compound becomes electrically conducting in the direction between the two components. In other directions the compound remains non-conducting (which makes it anisotropic).

A resin based on a plastic material like epoxy or acryl is more or less transparent for X-rays since such a material is made up of light atoms (low Z). In contrast, a conductive material like silver (high Z) interacts strongly with X-rays. Because the amount of conductive particles per volume unit of the anisotropic compound is low also the total weight or amount of conductive material per volume unit is low. And because only a small volume (i.e. a thin layer, typically with a thickness of some tens of µm) of the anisotropic compound is required to establish the desired electric connection, the total amount of conductive material needed for connecting the first conducting track and the first electrode can be kept very small; so small that its interaction with the X-radiation field becomes more or less negligible. The presence of (a thin layer of) non-conducting anisotropic compound at the sides of the conducting region of the compound does not have any significant effect on the interaction with the X-radiation field. The anisotropic conductive compound thus has the physical property of being close to transparent for X-rays (when applied in amounts that are sufficient for the application in question).

This is in contrast to the bonding of a gold wire to the electrode, where the bond (that typically contains tin and sometimes lead) of the gold wire can be clearly seen on an X-ray image of a detector device (as well as the gold wire itself). This is also in contrast to conventional isotropic conductive adhesives that contain large amounts (a high concentration) of a conducting material, such as Ag, that makes the material continuously conductive in all directions. Such an isotropic conductive material interacts very strongly with the X-ray field and if used as connection material it brings about a significant angle dependency of the detecting device, in similarity with the bonding of gold wires. Moreover, a small amount of such an isotropic conductive material is likely to cause undesired short circuits if applied on the wrong place, which is rather difficult to avoid since the components of concern here are very small (the X-ray sensing member may typically be 2 mm from edge to edge). An anisotropic conductive compound is not associated with the same disadvantage since it does not conduct electricity if not compressed sufficiently between the components.

The components to be connected via the anisotropic compound can be designed to make the compound properly conductive in a specific region, for instance by letting the first conductive track protrude from the surrounding surface of the substrate so that pressure is applied mainly or only along the first conductive track onto the anisotropic compound and further onto the first electrode when pressing the substrate and the sensing member together during production.

The anisotropic conductive compound may be in the form of a paste or liquid that can be deposited locally in certain positions, i.e. at certain isolated contact points, onto the sensing member or the substrate. Alternatively, the compound may be in the form of a film that may cover a larger portion of the sensing member or the substrate when applied thereto. A disadvantage of the film form is that very small pieces of film are usually difficult to handle, both manually and by automatic means. A further disadvantage of the film is that it may cover the intended contact points and make it more difficult to properly align the sensing member and the substrate in relation to each other before pressing them together. That is, the actual contact points may not be positioned exactly where they were intended to be positioned. In contrast, deposition of a paste or liquid can more easily be automated and it also becomes easier to arrange the contact points at their intended positions. To secure that the compound stays in place after deposition the viscosity of a liquid compound should not be too low. A paste may be regarded as a liquid with high viscosity.

Besides that a proper positioning of the contact points is important for the function of the device as a whole, establishing exact positioning of the contact points is important for making accurate data modelling/simulations of the device. Such simulations can e.g. be used for compensation of any remaining angular response dependency of the device and for designing or adjusting the energy filter for reducing the device's sensitivity to different X-ray energies.

Bonding of gold wires to the electrodes generally results in an uncertainty of the exact position of the contact point. As the present contacting technique provides for a more exact positioning of the contact points it provides an advantage in this regard compared to a structure as disclosed in e.g. WO2010/140944.

The use of a non-conducting substrate provided with one or more conducting tracks in combination with the anisotropic conductive compound simplifies the connection of the electrodes to the conductors compared to the use of gold wires. It also simplifies the handling of the composite component, i.e. the component including conductors+sensing member, since the gold wires easily breaks during handling, for instance in moments where the wires need to be bent and led through an openings in e.g. the outer support element or a casing of the device. A substrate that carries the conducting track, and in particular a flexible substrate, is less fragile and easier to handle. If the substrate is very thin and flexible a support may be arranged on the backside of the substrate, i.e. on the opposite side of the substrate in relation to the sensing member, to keep the substrate flat. At an edge of such a support, typically at a side of the sensing member, a flexible substrate can be bent without breakage of the conductive tracks, even if these tracks are thinner than a typical gold wire.

Moreover, gold wires are difficult to insulate electrically. At least for a working solid angle of close to 360° it would be difficult to avoid that a gold wire would come in contact with the supporting arrangement or the attenuation member. In contrast, conductive tracks arranged on one side of the non-conducting substrate are already insulated on the backside, i.e. on the opposite side of the substrate, and the front side of the substrate where the conductive track or tracks are arranged may be provided with a top layer of an insulating material (except at the sensing member where electric connection is desired).

The term "semiconducting X-ray sensing member" refers to a semiconducting component configured to function as an X-ray sensor, i.e. it has semiconducting properties and is capable of generating an electric signal when exposed to X-radiation. The sensing member is sometimes denoted sensor element, detecting member or simply detector. An example of a semiconducting X-ray sensing member suitable for the present invention is disclosed in WO2010/140944. The semiconducting X-ray sensing member typically has a main body comprising doped silicon, a diffusion zone forming part of the main body, highly doped electrode surfaces, and a non-conducting oxide passivation zone arranged between the two electrodes.

The X-ray sensing member should be as free as possible from high-z material that attenuates X-radiation and affects the measurement. This is in contrast to traditional sensor elements and other types of semiconducting components that have connectors and backplane with high z material (e.g. lead or tin) and that may have connectors on both sides of the element. Such elements and components disturb the measured signal, in particular in CT/CBCT applications where 4 Pi detectors are preferable.

In an embodiment of the invention the non-conducting substrate is arranged at the surface of the X-ray sensing member and extends substantially in parallel with said surface. The substrate has a first side facing the X-ray sensing member and a second, opposite side facing away from the X-ray sensing member, wherein the first conducting track is arranged on the first side of the substrate.

In an embodiment of the invention the first and second electrodes are arranged on the same main surface of the X-ray sensing member, wherein the substrate is provided with a second conducting track that forms the second electric conductor, wherein also the connection between the second conducting track and the second electrode is arranged by means of an anisotropic conducting compound. Thus, a single substrate can be used for connecting both electrodes. The two conducting tracks are electrically insulated from each other.

In an embodiment of the invention the first and second electrodes are arranged on opposite main surfaces of the X-ray sensing member, wherein the device comprises a further non-conducting substrate provided with a further conducting track, wherein the further substrate is arranged at the second main surface of the X-ray sensing member and extends substantially in parallel with said second main surface, and wherein the further conducting track forms the second electric conductor. This use of two substrates, one on each side of the sensing member, provides for the possibility to apply the combination of conductive tracks arranged on a non-conductive substrates and a anisotropic compound to conventional semiconducting X-ray sensing member with electrodes on opposite sides.

In an embodiment of the invention the X-ray sensing member is provided with at least one electrode contact point substantially free from surface oxides. The contact point may be covered with a thin layer of titanium nitride. Compared to a contact cover layer of gold, this provides for a better adhesion to the anisotropic conductive compound and there is less interaction with the X-radiation.

In an embodiment of the invention the anisotropic conductive compound is positioned locally at the at least one electrode contact point. The anisotropic conductive compound is applied onto the sensing member or the substrate before connecting the two components. Although a film-type compound may be applied over a larger area of the component, local deposition of a paste-type compound requires less amounts of the compound. Deposition/dispensing of a paste compound can be made with high precision and accuracy. Such local positioning of the compound also simplifies alignment of the two components (before pressing them together) since a film will cover the conductive tracks on the substrate or the contact points on the electrode(s).

In an embodiment of the invention the X-ray sensing member is provided with a plurality of spaced-apart electrode contact points, wherein the anisotropic conductive compound is positioned locally at each of said plurality of spaced-apart electrode contact points so as to form isolated contact point regions containing the compound and to form a space substantially free from the compound between the contact point regions. Preferably, the X-ray sensing member is provided with at least three electrode contact points that are laterally distributed over the surface of the X-ray sensing member in a pattern that defines support positions adapted to the size and shape of the non-conducting substrate so as to, when the anisotropic conductive compound is positioned locally at each of said at least three electrode contact points, provide a support for the non-conducting substrate. With such distributed support points the substrate and the sensing member surface are more likely to stay parallel to each other during the manufacturing process.

In an embodiment of the invention the surface of the X-ray sensing member has a substantially rectangular shape and wherein the plurality of electrode contact points comprises four corner contact points arranged at each corner of the rectangular surface and one central contact point arranged in a central region of the rectangular surface. This forms a suitable distribution of the support points. The four corner points may form contacts for one of the electrodes and the central point may form a contact for the other electrode (one electrode surface may form a frame around the other electrode surface located centrally on the rectangular sensing member surface). The single central contact point may be larger than the individual corner contact points. All five contact points may form contact points to the same electrode, typically in the case where the electrodes are arranged on opposite sides of the sensing member.

In an embodiment of the invention the first and second electric conductors are connected to electronic equipment configured for handling of an output signal from the X-ray sensing member, such as an electrometer.

In an embodiment of the invention the non-conducting substrate is made of a plastic or ceramic material, preferably a flexible plastic material. The non-conducting substrate has a thickness in the range 25-200 µm.

In an embodiment of the invention the device comprises a substrate supporting member comprising a flat surface arranged at a side of the non-conducting substrate that faces away from the X-ray sensing member. This can be used to keep the substrate flat to secure an appropriate electric connection etc.

In an embodiment of the invention the first conducting track is raised, preferably in the range 5-50 µm, in relation to a surrounding substrate surface. The first conducting track may be made of copper. An example of another suitable material is aluminum.

In an embodiment of the invention the anisotropic conductive compound comprises conductive particles distributed in a non-conducting resin or matrix material, wherein the compound is non-conducting unless the conductive particles are brought together. Preferably, the anisotropic conductive compound comprises a thermosetting resin.

In an embodiment of the invention at least one, preferably each, main side of the X-ray sensing member is provided with a flat inner attenuation member that extends alongside of the main side. Such an inner attenuation member may be used to further adjust any angular dependency, typically an angular dependency originating from the asymmetric shape of the sensing member (large, wide and thin main surfaces vs. small, narrow and deep edges). Exactly which shape and material to choose for the inner attenuation members depends on the X-radiation to be measured, the outer (main) energy filter and the sensing member. The inner attenuation member may be provided with inner low-attenuation zones, such as through-holes, with a similar function as described above. In general, the shape of the inner attenuation member may be a thin top-slice of a sphere (a spherical cap) with a diameter roughly the same as the edge of the sensing member and with a maximum thickness (at its center point) less than that of the sensing member. Where a non-conducting substrate provided with a conducting track is arranged at the sensing member, the flat side of the inner attenuation member may provide a support for the substrate (i.e. the substrate is positioned between the sensing member and the inner attenuation member). The inner attenuation member may be made of stainless steel. An open cavity adapted to receive the rounded side of one of the inner attenuation members may be arranged in the inner supporting element.

BRIEF DESCRIPTION OF THE FIGURES

In the description of the invention given below reference is made to the following figure, in which.

DETAILED DESCRIPTION OF VARIOUS EMBODIMENTS

Figure 1:
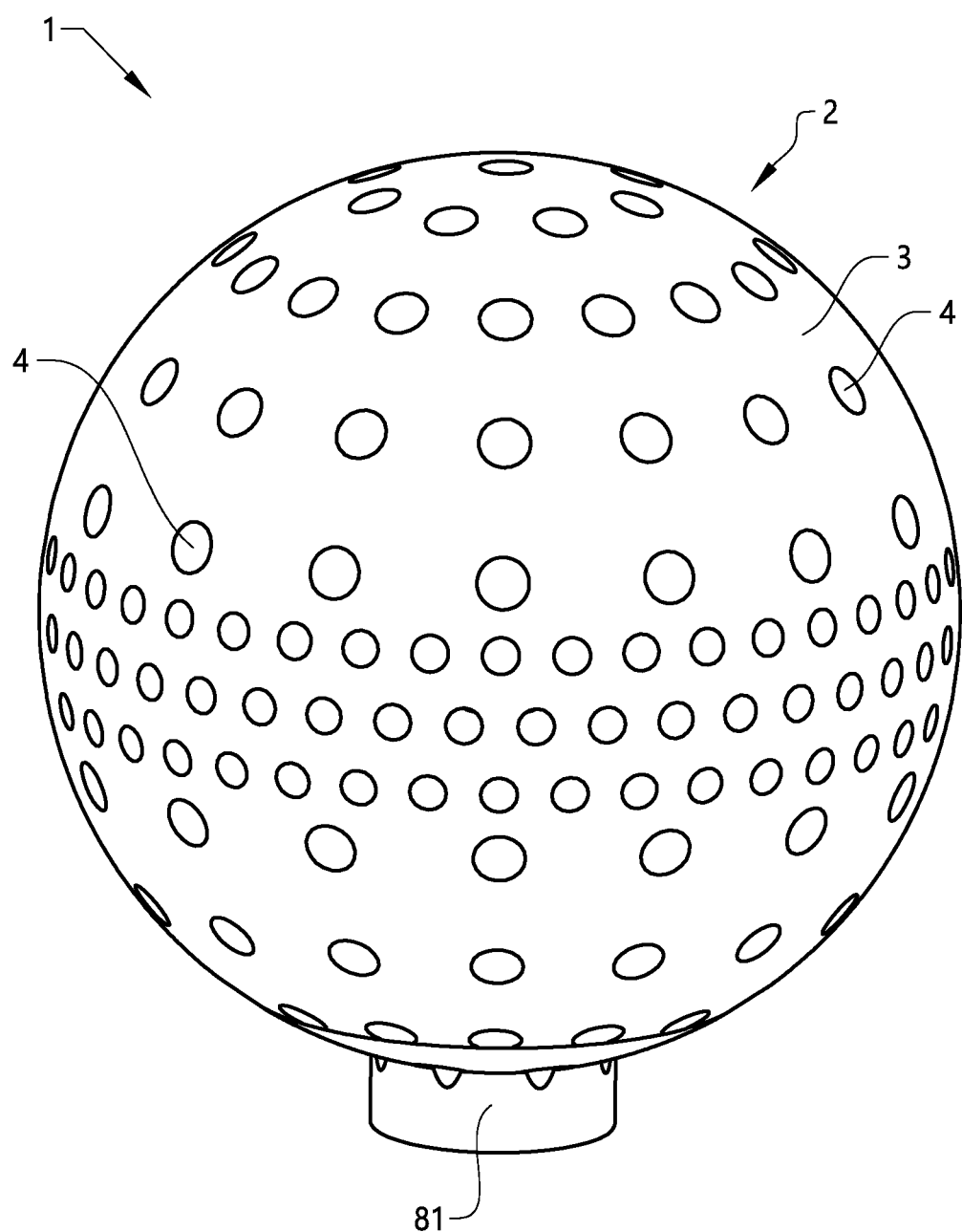
FIG. 1 shows, in a perspective view, an embodiment of a detection device according to the invention.

FIGS. 1-5 shows different (part) views of the same embodiment of an X-ray detection device 1 according to the invention. This embodiment is an example of a detector/sensing member provided with a 4π energy filter useful for being arranged in an aluminum cylinder for use in CT applications in line with the device described in WO2010/140944. The embodiment shown in FIGS. 1-5 can be used as a 4π reference dose meter in diagnostic radiology QA and QC. It can also be used as a general 4π point dose detector for clinical use in diagnostic applications. Other embodiments are of course possible.

The exemplified X-ray detection device 1 comprises an X-ray sensing member 10 (see FIGS. 2-5) and an X-ray energy filter 2 comprising a spherical attenuation member 3 made of stainless steel that attenuate low-energy X-rays to a greater extent than high-energy X-rays in a beam or field of X-radiation directed towards the X-ray sensing member 10.

The attenuation member 3 is arranged to extend in a spatial manner around the X-ray sensing member 10 so as to subtend a working solid angle of 360° (4π sr, steradian) in relation to the X-ray sensing member 10. The attenuation member 3 is provided over a spherical working area corresponding to the working solid angle with a plurality of low-attenuation zones in the form of circular through-holes 4 through the attenuation member 3 distributed over the working area of the attenuation member 3. The low-attenuation zones/through-holes 4 attenuate X-rays only to a small or negligible extent so as to allow passage of both low-energy and high-energy X-rays to a substantially similar extent through the attenuation member 3 towards the X-ray sensing member 10.

The through-holes 4 are distributed in relation to the X-ray sensing member 10 in such a way that, when the X-ray detection device 1 is exposed to a beam or field of parallel X-radiation that is directed towards the X-ray sensing member 10 within the working solid angle (i.e. in any direction in this case) and that has a width that covers a projected area of the energy filter 2 (i.e. it covers at least the diameter of the sphere in this case), only a first portion (around 25% in this case) of a total surface of the X-ray sensing member 10 facing the beam or field of X-radiation is directly exposed to low-attenuated X-rays that pass through the through-holes 4. A second remaining portion (i.e. around 75% in this case) of the total surface of the X-ray sensing member 10 facing the beam or field of X-radiation is directly exposed only to X-rays that pass through the attenuation member 3, i.e. between the through-holes 4.

Further, the relation between i) the first portion (25%) of the total surface of the X-ray sensing member 10 facing the beam or field of X-radiation and ii) said total surface of the X-ray sensing member 10 facing the beam or field of X-radiation, is substantially constant (i.e. around 1:4 in this case) irrespective of a spatial angle of incidence of the beam or field of X-radiation that falls within the working solid angle, i.e. any angle of incidence in this case.

For example, irrespective of whether the X-radiation is directed downwards, upwards, from left to right, from right to left, etc. towards the sensing member 10 (in relation to FIG. 1), the same portion (25%) of the total surface of the X-ray sensing member 10 facing the X-radiation will form a direct target surface for X-radiation passing through the through-holes 4. This evens out the detection energy response (since X-rays of lower energy, which are detected with a higher efficiency than X-rays of higher energy by the sensing member 10, are blocked by the attenuation member 3 to a higher extent) and since this is done consistently over the working solid angle (360°) irrespective of the direction of the X-radiation (within the working solid angle), this provides for the possibility to design the more detailed structure of the attenuation member 3 and the low-attenuation zones 4. This detailed structure depends, for instance, on the type and shape of the sensing member and the energy distribution of the X-radiation to be used.

In this case where: i) the sensing member 10 is a semi conducting detector (N-doped Si) with a flat rectangular shape having the nominal dimensions 2400×2400×350 um and being arranged centrally in a spherical energy filter 2; ii) the attenuation member 3 is spherical; and iii) all channels through the attenuation member 2 formed by the through-holes 4 are straight and directed towards a center point of the spherical attenuation member 3; the following forms an example of suitable parameters for X-radiation with an energy distribution corresponding to, for instance, an RQT beam quality standard according to IEC 61267 (Medical diagnostic X-ray equipment—Radiation conditions for use in the determination of characteristics), which is suitable for CT applications:

Attenuation member 3:
Material: Stainless steel
Outer diameter of sphere: 7.0 mm
Thickness (radial direction): 1.0 mm
Low-attenuation zones/through-holes 4:
Diameter of individual holes primarily directed towards the edge of the sensing member 10 (i.e. the smaller holes 4 along the "equator" of the attenuation member 3): 0.282 mm
Distribution of individual holes along "equator": three parallel rows; 9° radial angle between holes
Diameter of remaining individual holes primarily directed towards the main flat surfaces of the sensing member 10 (i.e. the larger holes 4 on the "upper/northern and lower/southern hemisphere" of the attenuation member 3): 0.4 mm
Distribution of individual holes on "northern and southern hemisphere": 18° radial angle between holes in both directions Other sizes and distributions of through-holes 4 may also be suitable. For instance, the pattern of holes 4 directed towards the sensing member edge along the "equator" of the attenuation member 3, i.e. a pattern where the holes are smaller but located closer to each other compared to the rest of the attenuation member 3, is likely to be useful over the entire attenuation member 3. However, an increased total number of holes complicates computer simulation of the device 1. It may also make the production more complex. In contrast, the pattern of larger and more spaced-apart holes 4 used on the upper and lower parts of the attenuation member 3 is not suitable along the "equator" since a too large portion of the (edge of the) sensing member 10 would form a direct target area through such large holes when the X-radiation is directed towards the edge in parallel with the main surfaces of the sensing member 10.

Figure 2:
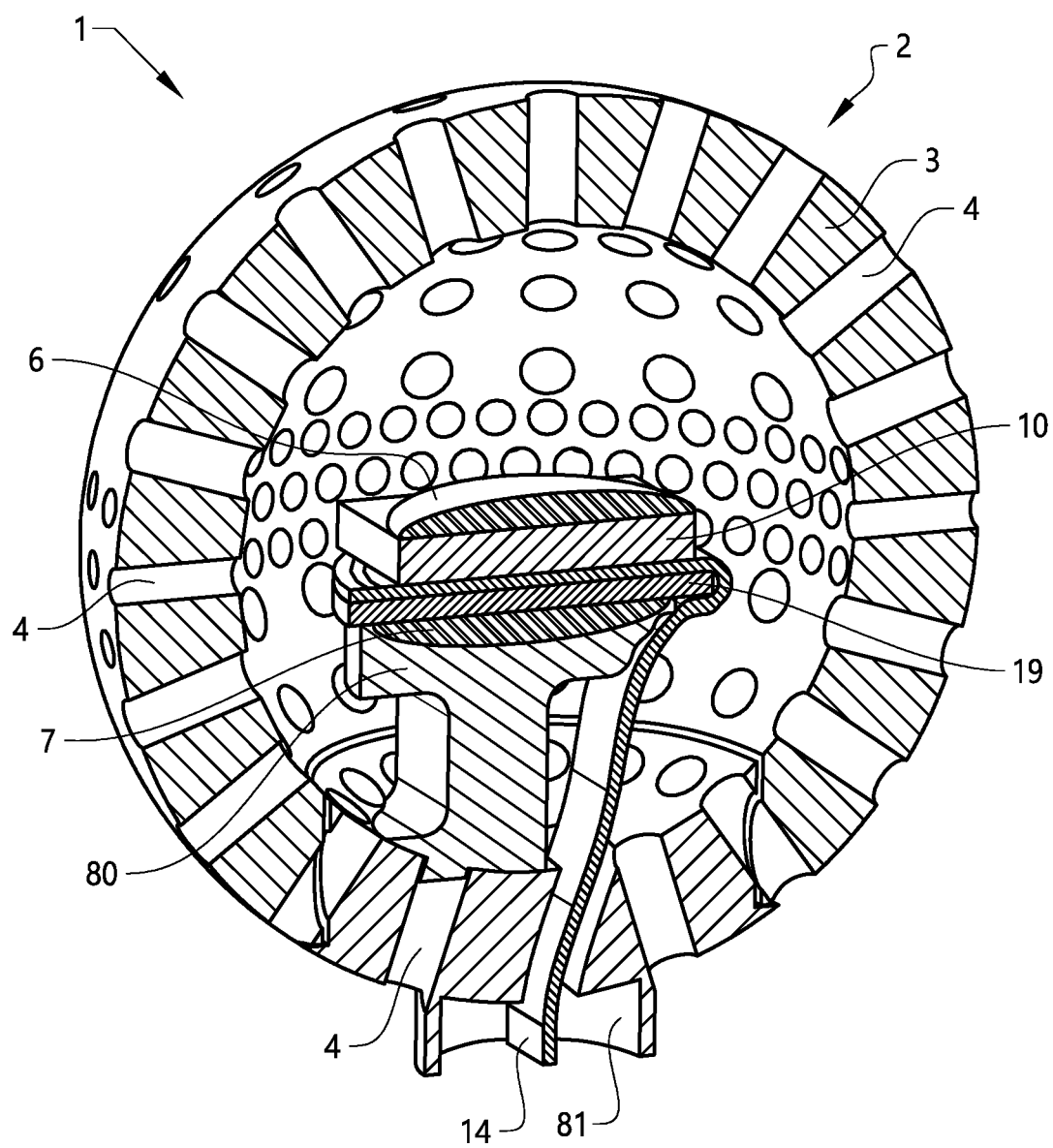
FIG. 2 shows a sectional view of the embodiment according to FIG. 1.
Figure 3:
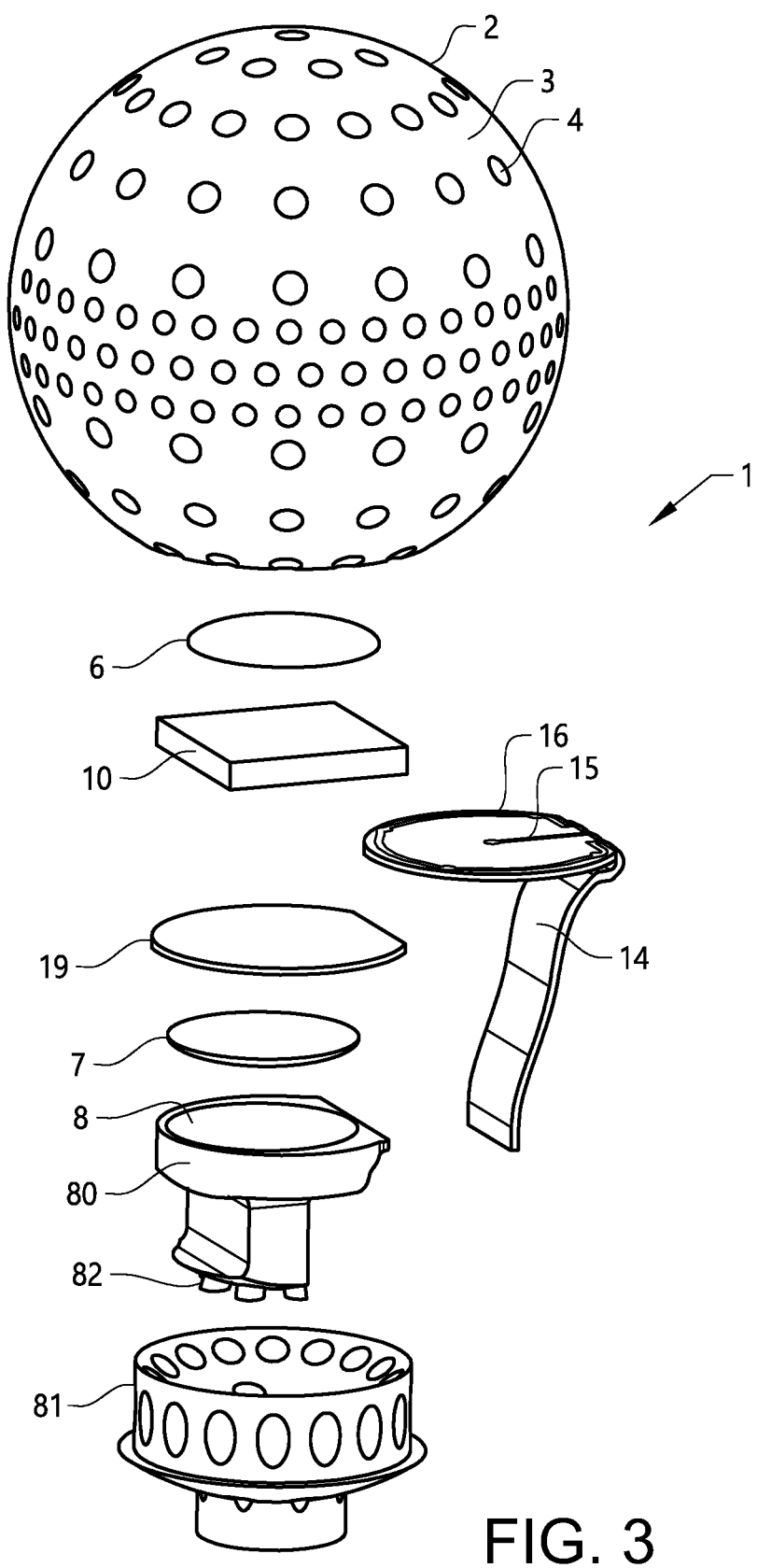
FIG. 3 shows an exploded view of the embodiment according to FIG. 1.
Figure 4:
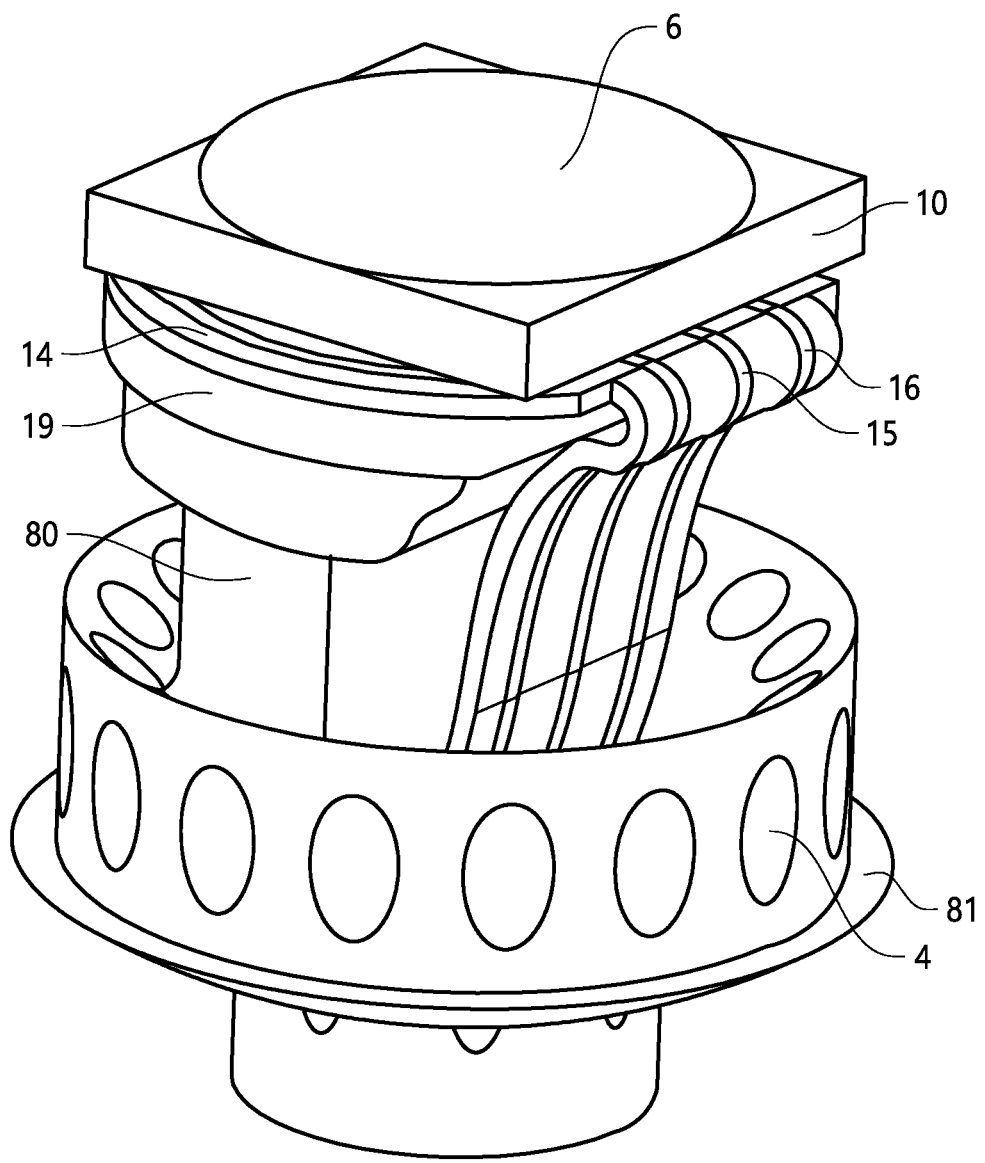
FIG. 4 shows the arrangement of the X-ray sensing member of the embodiment according to FIG. 1.

FIGS. 2-3 show that the exemplified detection device 1 comprises: the energy filter 2, in turn comprising the attenuation member 3 and the through-holes 4; first and second inner attenuation members 6, 7; the X-ray sensing member 10; a non-conducting substrate 14 provided with first and second conductive tracks 15, 16; a substrate support 19; an inner support element 80 provided with an open cavity 8 adapted to receive a rounded lower side of the second inner attenuation member 7; and an outer support element 81 provided with through-holes 4 and forming part of the attenuation member 2.

The first and second inner attenuation members 6, 7 are optional but may be used to adjust primarily the angular dependency of the detection device 1. As can be seen in the figures, each inner attenuation member 6, 7 has a flat side facing the sensing member 10 and a rounded side facing away from the sensing member 10. The flat side of the second inner attenuation member 7 forms a flat support for the substrate 14 and the sensing member 10. In case no inner attenuation members 6, 7 are present the cavity 8 may be dispensed with and the upper side of the inner support element 80 facing the sensing member 10 may be flat.

The substrate 14 the electric connection to the sensing member 10 is described below in relation to FIG. 5.

The substrate support 19 is typically fixed to the substrate 14 before assembling the detection device 1. Its purpose is to support and stabilize the substrate 14 at the sensing member 10 since the substrate is very thin and flexible.

The inner support element 80 is connectable to the outer support element 81 via feet 82 adapted to fit into through-holes 4 in the outer support element 81. The outer support element 81 is connectable to the main part of the attenuation member 3 so as to, when connected, form an attenuation member 3 with a 360° solid angle in relation to the X-ray member 10. As the inner and outer support elements 80, 81 are properly connected the sensing member 10 is positioned in the center of the spherical attenuation member 3. The inner support element 80 is made of a plastic material that has a negligible influence on X-radiation directed towards the sensing member 10. The outer support element 81 is made of stainless steel (same as the main part of the attenuation member 3).

As an alternative to what is shown in the figures, the inner and outer support elements 80, 81 may form an integral component. By designing such an integrated inner support element in a threadlike manner and with passages corresponding to the through-holes 4 in the outer support element 81, the interaction of the integrated inner support element with the X-radiation can be made negligible or at least sufficiently small.

The attenuation member 2, the outer support element 81 and the inner support element 80 (if integrated with the outer support element 81) may all be made in stainless steel and produced by additive manufacturing (3D printing).

The X-ray sensing member 10 has a flat rectangular shape with first and second main, substantially parallel surfaces facing downwards and upwards, respectively, in the figures. A sensing member perimeter edge faces sideways. First and second electrodes 11, 12 are both arranged at the first (lower) main surface of the X-ray sensing member 10. An electrically non-conducting oxide passivation zone 13 is arranged between the electrodes. The second electrode 12 forms a frame around the central first electrode 11.

Figure 5:
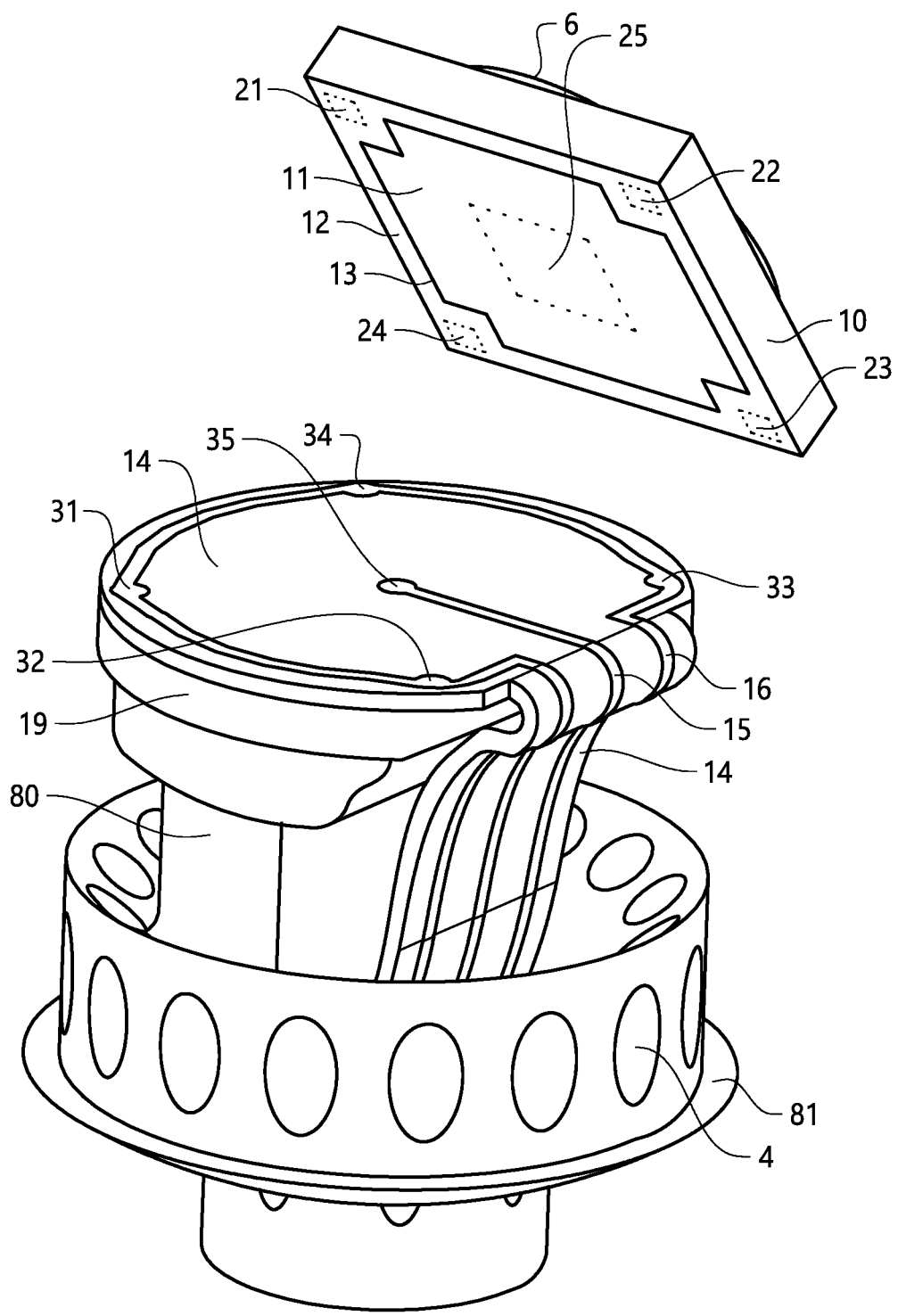
FIG. 5 shows the arrangement according to FIG. 4 in a partly dissembled state 1.

The X-ray sensing member 10 is associated with a non-conducting substrate 14 provided with first and second conducting copper tracks 15, 16 (see in particular FIG. 5). The first and second conducting tracks 15, 16 form first and second electric conductors connected to the first and second electrodes 11, 12, respectively. As will be described below in relation to FIG. 5, the connection between the conducting tracks 15, 16 and the corresponding electrodes 11, 12 is arranged by means of an anisotropic conducting compound 31-35.

The non-conducting substrate 14 is arranged at the first (lower) main surface of the X-ray sensing member 10 and extends substantially in parallel with said surface. The substrate 14 comprises a part that extends away sideways from the X-ray sensing member 10, is bent, and extends further along the inner support element 80 towards the outer support element 81 and through the outer support element 81 via an opening thereof (see FIG. 2) and further away from the device 1 (downwards in the figures). The entire extension of the substrate 14 away from the device 1 is not shown in the figures. The conductive tracks 15, 16 are arranged onto the substrate 14 and extend away in the same manner. The conductive tracks 15, 16, and thus the electrodes 11, 12, are, at some distance from the detection device 1, connected to electronic equipment (not shown in the figures) configured for handling of an output signal from the X-ray sensing members, such as an electrometer.

The substrate 14 has a first side facing the X-ray sensing member 10 (upwards in the figures) and a second, opposite side facing away from the X-ray sensing member 10 (downwards in the figures). The conducting tracks 15, 16 are arranged on the first side of the substrate 14.

The X-ray sensing member 10 is in this example provided with five spaced-apart electrode contact points 21-25 (see FIG. 5) which have been made substantially free from surface oxides. The electrode contact points comprises four corner contact points 21-24 arranged at each corner of the rectangular surface for connection to the second electrode 12 of the sensing member 10. A single, but in this case larger, central contact point 25 is arranged in a central region of the rectangular surface for connection to the first electrode 11. The electrode contact points 21-25 are thus laterally distributed over the surface of the X-ray sensing member 10 in a symmetric pattern that defines support positions for the non-conducting substrate 14.

The pattern of the contact points 21-25 on the one hand and the size and shape of the substrate 14 and the conducting tracks 15, 16 on the other hand, are adapted to each other so that an appropriate electric connection can be established between the electrodes 11, 12 and the conducting tracks 15, 16.

The anisotropic conductive compound, indicated as local regions 31-35 in FIG. 5, is positioned locally (by dispensing the compound in paste form) at each of the five electrode contact points 21-25 so as to form isolated contact point regions containing the compound and to form a space substantially free from the compound between the contact point regions. In contrast, an anisotropic conductive compound of the film type would have formed a layer covering also the area/space between the contact points.

During production the anisotropic compound may be applied either onto the electrode contact points 21-25 or in corresponding positions 31-35 onto the first side of the substrate (or rather onto the conductive tracks in these positions). FIG. 5 illustrates that the compound has been applied onto the substrate 14 (or rather onto the conductive tracks 15, 16 arranged on the substrate 14) and not onto the electrode contact points 31-35. When the device 1 has been assembled it may be that it is difficult to see onto which component the compound has been applied.

When the anisotropic compound has been applied in the proper positions, the substrate 14 and the sensing member 10 are pressed together and exposed to heat for some period of time. During cooling the compound hardens. The conducting tracks 15, 16 are raised in relation to the surrounding substrate surface, as an example by 18 µm, which means that the pressure is generated only or mainly along the conductive tracks 15, 16 and that the compound gets conductive only if present along the conductive track, i.e. at the contact points in this case. The heat cures the thermosetting resin in the compound and fixes the substrate 14 to the sensing member 10. The distributed pattern of the contact points 21-25 (31-35) results in a good support for the non-conducting substrate 14, which is particularly useful during the pressing and heating process.

The non-conducting substrate 14 is in this case made of a flexible plastic material and has a total thickness of around 100 µm, including protection layers (not shown in the figures). Protection layers are preferably applied onto the entire part of the substrate 14 except at the sensing member 10 where electric contact is to be established with the conducting tracks 15, 16, i.e. the substrate 14 is covered with a protection layer from the bent part and away from the sensing member 10 and the device 1 (i.e. from the bent part and downwards in the figures). The protection layer prevents, for instance, electric short-circuit contact between the conductive tracks 15, 16 and the outer support element 81. The non-conducting substrate 14 may be based on polyimide with a thickness of 50 um (without protection layer). Local contact pads/points/areas on the substrate 14 at positions 31-35 may be prepared by adding 3-6 μm Ni and 0.056 μm Au.

The non-conducting substrate 14 is in this example provided with the substrate supporting member 19 comprising a flat surface arranged (glued) at the second side of the substrate 14. The substrate supporting member 19 may have a thickness of 150 μm.

The method of connecting first and second electric conductors to first and second electrodes of an X-ray sensing member may comprise the following steps: providing the semiconducting X-ray sensing member 10 having first and second electrodes 11, 12; providing the non-conducting substrate 14 provided with at least a first conducting track 15 that forms the first electric conductor; applying an anisotropic conducting compound onto the first electrode 11 or onto the substrate 14 at the first conducting track 15; positioning the X-ray sensing member 10 and the substrate 14 in relation to each other and pressing them together so as to establish an electric connection between the first conducting track 15 and its corresponding electrode 11 via the anisotropic conducting compound.

The method may further comprise one or several of the following steps: preparing at least one contact point 25 at the surface of the first electrode 11; dispensing the anisotropic conducting compound locally onto one or several contact points 21-25 at the surface of the first electrode 11 or onto the substrate 14 and the first conducting track 15 in positions 31-35 corresponding to the electrode contact points 21-25; heating the X-ray sensing member 10 and the non-conducting substrate 14 while pressing them together.

Heating is carried out during a sufficient time period. A few seconds may be sufficient. A thermosetting compound hardens during cooling.

A method of manufacturing the entire device 1 may comprise additional steps such as: producing the attenuation member 3 by means of additive manufacturing; producing the outer support element 81, optionally together with an integrated inner support element 80, by means of additive manufacturing; after having established the electric connection between at least the first conducting track 15 and its corresponding electrode 11 via the anisotropic conducting compound and thereby having formed a combined substrate-sensor component, fixing the substrate-sensor component onto the inner support element, optionally via the second inner attenuation member 7, using an adhesive; arranging the extending part of the substrate 14 through an opening in the outer support element 81; connecting the attenuation member 3 and the outer support element 81.

Figure 6:
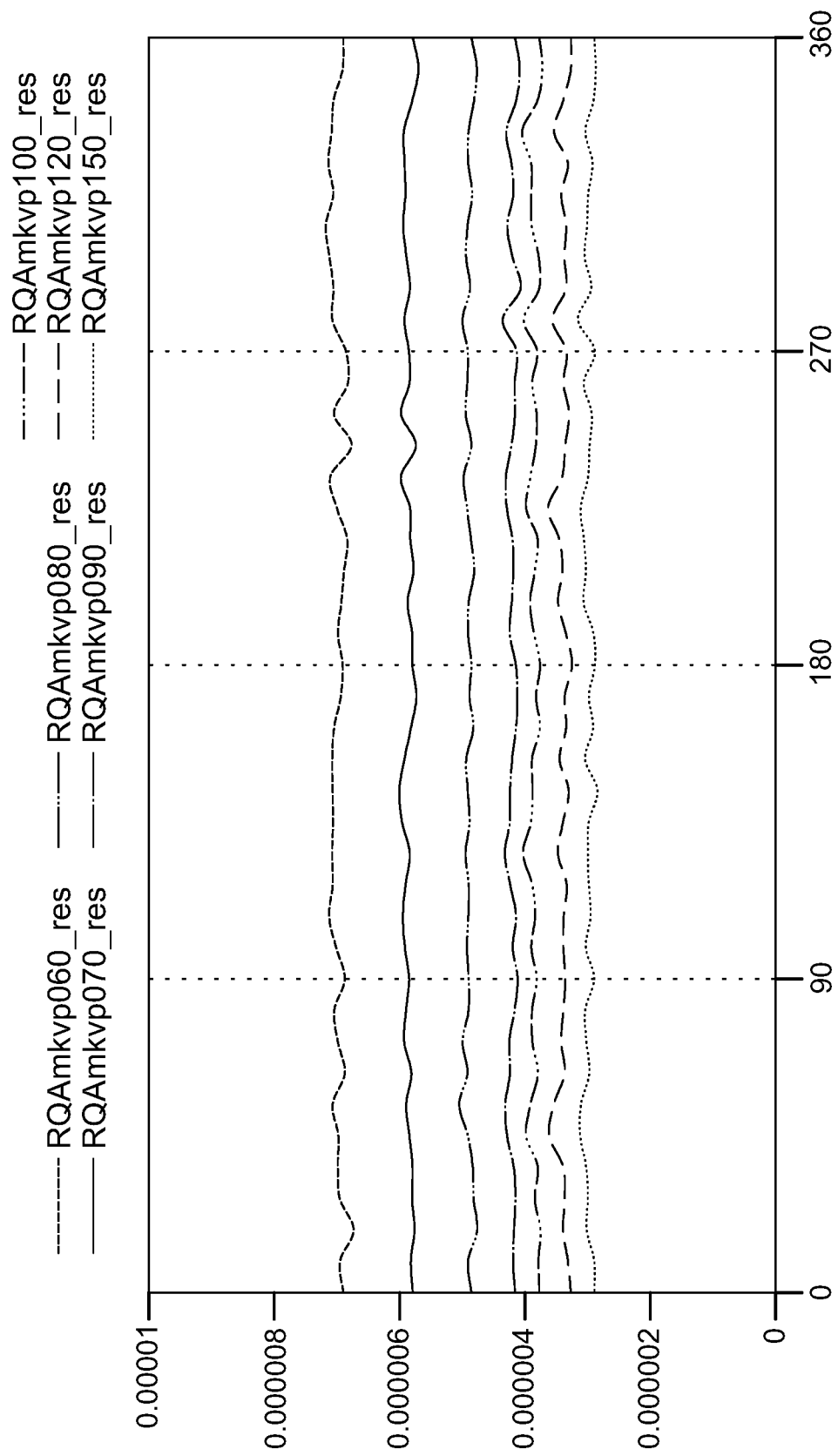
FIG. 6 shows a relative energy response for a sensing member as a function of rotational position in a first plane along an edge of the sensing member.
Figure 7:
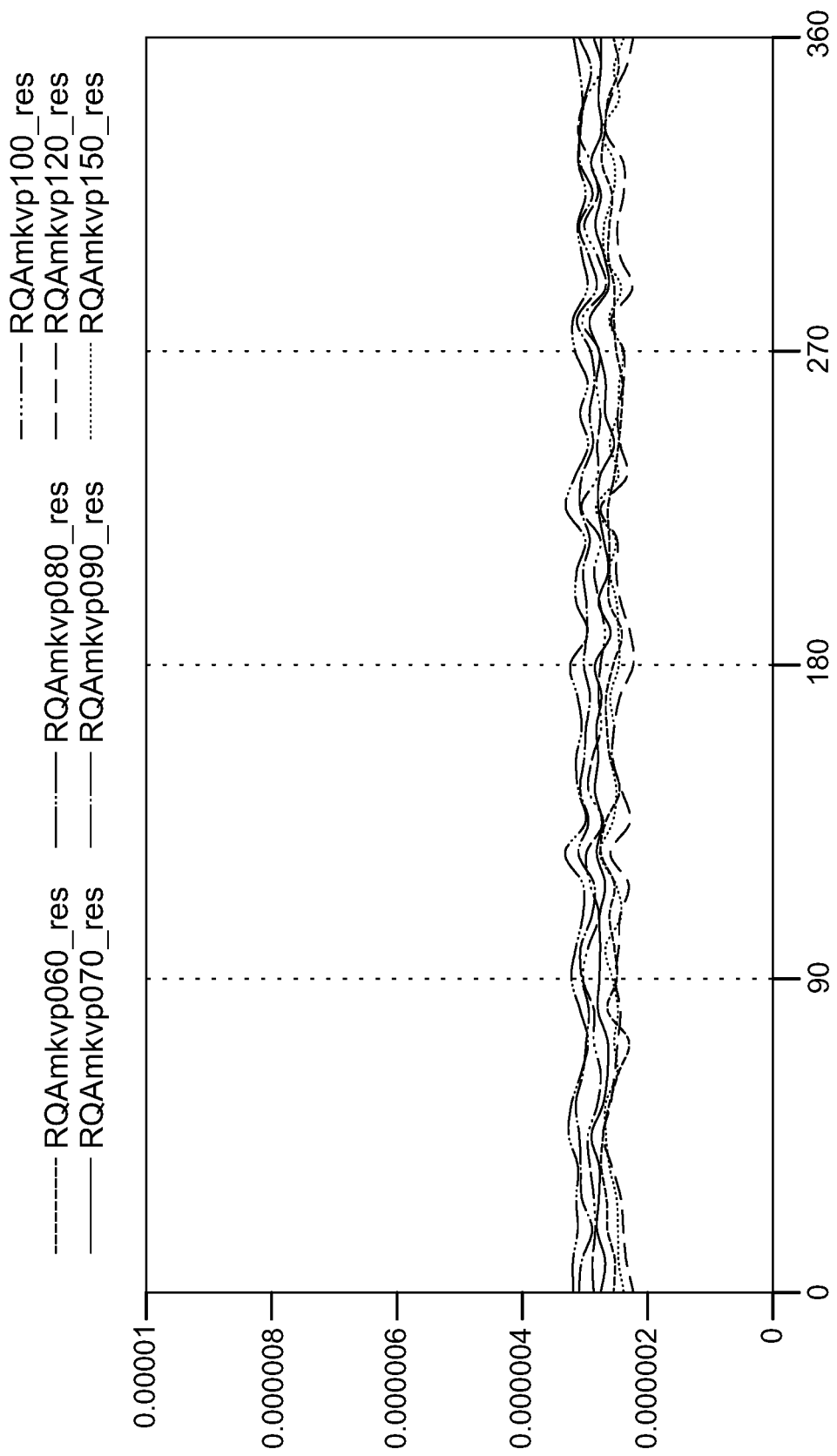
FIG. 7 shows a relative energy response in the first plane for the sensing member of FIG. 6 where the sensing member is provided with an energy filter.
Figure 8:
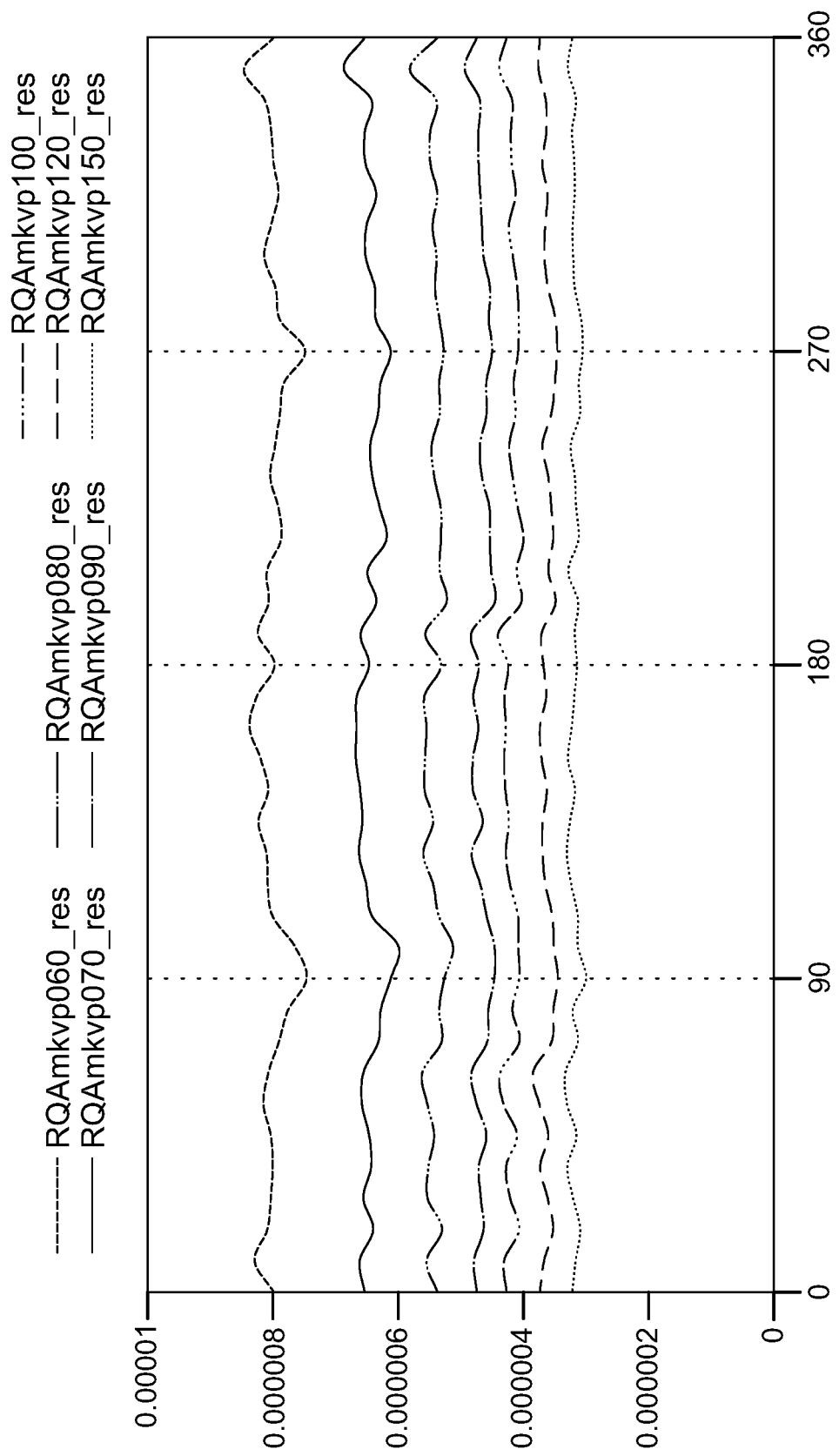
FIG. 8 shows a relative energy response for the sensing member of FIG. 6 as a function of rotational position in a second plane perpendicular to the first plane.
Figure 9:
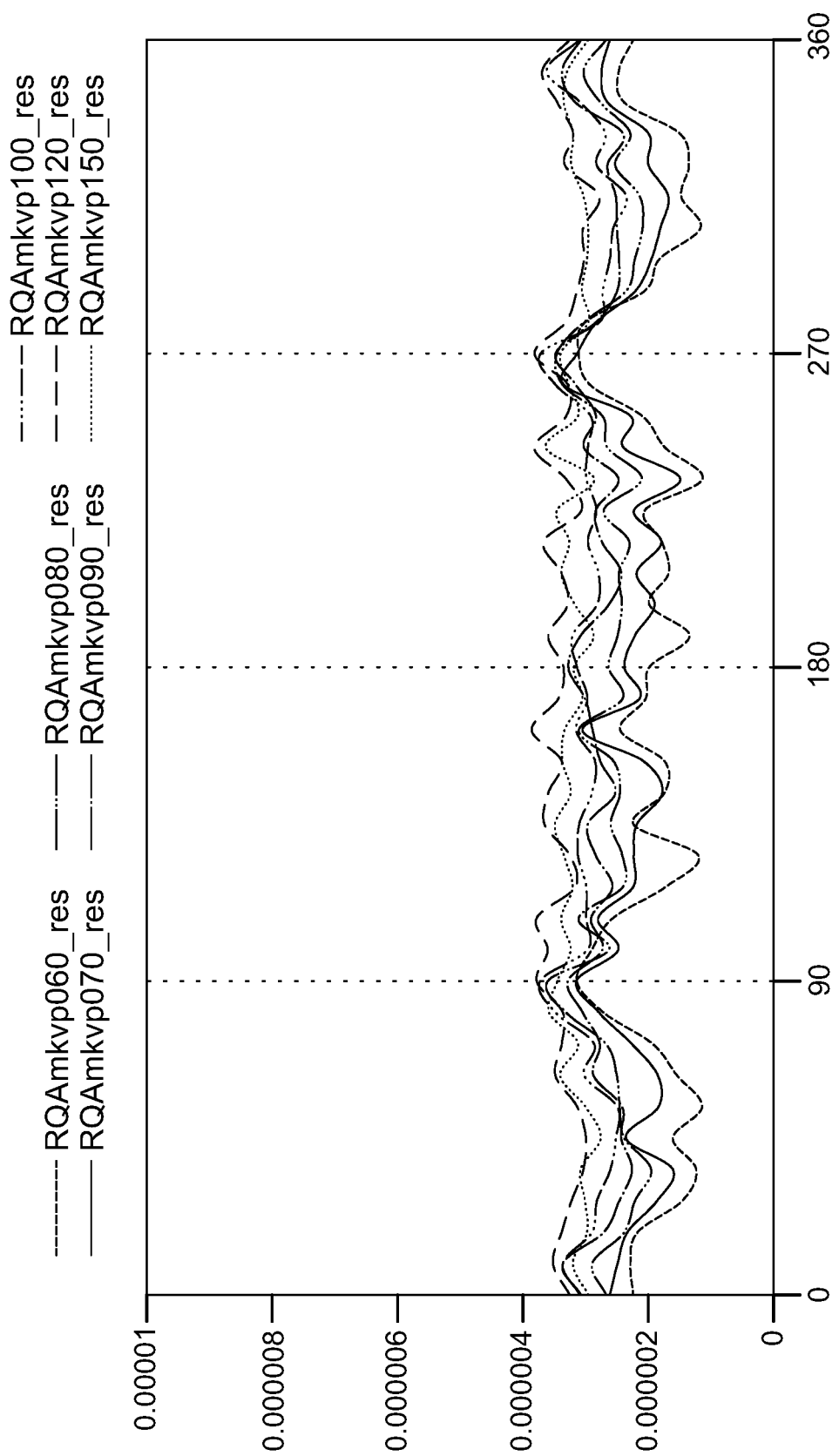
FIG. 9 shows a relative energy response in the second plane for the sensing member of FIG. 8 where the sensing member is provided with an energy filter.

FIGS. 6-9 show simulated relative energy responses for the X-ray sensing member 10 as a function of rotational position in a first plane (along the edge of the sensing member; FIGS. 6 and 7) and in a second plane perpendicular to the first plane (FIGS. 8 and 9). The x-axis shows the rotational position in the plane (0-360°) and the y-axis shows the resulting relative energy response (arbitrary units). The different standard X-ray energy distributions used are given in each figure. The calculations were made in steps of 9°.

FIGS. 6 and 8 show the results for the X-ray sensing member 10 alone without any energy filter. These figures thus show the relative energy response in different angles for the sensing member 10 itself.

FIGS. 7 and 9 show the results for the X-ray sensing member 10 in the presence of the energy filter 2, i.e. the sensing member 10 is placed inside the spherical attenuation member 3 as shown in FIGS. 1-5. The flat inner attenuation members 6, 7 are not included in the simulations and their effect is not included in the results shown in FIGS. 6-9. Except for the inner attenuation members 6, 7, the results in FIGS. 7 and 9 relate to an entire detection device according to the figures, i.e. including the attenuation member 2, the through-holes 4, the substrate 14 (including the conductive tracks 15, 16, the anisotropic conductive compound and the contacts) and the inner and outer support elements 80, 81. The simulations also include PMMA and an aluminum cylinder that surround the energy filter 2 and the sensing member in line with what is shown in WO2010/140944 (which, however, has only a minor effect on the results).

In FIGS. 6 and 7 the X-radiation is simulated to be directed towards the edge of the X-ray sensing member 10 in a first plane parallel with the main surfaces thereof. At 0° the radiation is directed perpendicular to a first edge, at 45° the radiation is directed towards a corner between the first and second edge, at 90° the radiation is directed perpendicular to the second edge, and so on until one revolution is completed at 360°.

In FIGS. 8 and 9 the direction of the X-radiation is simulated to be rotated in a second plane perpendicular to the first plane used in FIGS. 6 and 8 (and thus perpendicular to the main surfaces of the sensing member 10), where the second plane intersects with the sensing member at a center point thereof and where the second plane is parallel with two of the sensing member edges and perpendicular to the other two edges. At 0° in FIGS. 8 and 9, the radiation is simulated to be directed towards the lower main surface of the X-ray sensing member 10, where "lower" refers to how the sensing member is shown in the figures. For FIG. 9 this means the radiation is directed through the outer and inner support elements 80, 81 (and partly through the holes 4 in the outer support element 81). At 90° the radiation is directed towards an edge of the sensing member 10 parallel with the main surfaces, at 180° the radiation is directed towards the upper main surface of the X-ray sensing member 10, at 270° towards an opposite edge, until one revolution is completed at 360°. For FIG. 9 the radiation is simulated to pass the energy filter 2 before reaching the sensing member 10.

The different energies RQAmkvp060 etc. correspond to different standards. For the purpose of FIGS. 6-9 it is sufficient to note that the different curves represent different X-ray energy distributions and that RQAmkvp060 has the lowest X-ray energies and RQAmkvp150 has the highest energies.

The embodiments of the detection device shown in FIGS. 1-5 and used in the simulations shown in FIGS. 6-9 are not optimized for the (low) energies in the RQA-standards. However, simulations based on RQA (including RQA with lower energies) shows clearly the effect of the detection device of this disclosure.

FIG. 6 shows that the relative response of the sensing member in the first plane (along the edge) varies considerably without the energy filter; the relative response is around 0.000007 for the lowest energies and around 0.000003 for the highest energies.

FIG. 7 shows that the energy filter 2 has significantly reduced and almost eliminated the energy response dependency in the first plane to a value of around 0.0000025-0.000003 for all energies.

FIGS. 6 and 7 further show that the angular response dependency in the first plane is relatively low (the curves are fairly flat and straight).

FIG. 8 shows that the relative response of the sensing member in the second plane (towards the main surfaces of the sensing member at 0° and 180°) also varies considerably without the energy filter; the relative response is around 0.000008 for the lowest energies and around 0.000003 for the highest energies.

FIG. 9 shows that the energy filter 2 has significantly reduced and almost eliminated the energy response dependency also in the second plane to a value of around 0.000002-0.000003 for all energies (except for the lowest energy RQAmkvp060).

FIGS. 6 and 7 further show that the angular response dependency also in the second plane is relatively low (at the curves for the higher energies are fairly flat and straight).

The energy filter 2, i.e. the attenuation member 3 and the through-holes 4, thus has the effect of significantly reducing the energy response dependency of the detection device 1. And since the detection device 1 also has a very small angular response dependency it is very useful for 4π dose measurements.

The invention is not limited by the embodiments described above but can be modified in various ways within the scope of the claims. For instance, the energy filter may be structured in a different way as already indicated above. An example is that the working solid angle may be less than 360°, for instance 180° (hemisphere), and in such a case it may not be important that any outer support element 81 forms part of the attenuation member 3. Another example is that the individual low-attenuation regions 4 may exhibit a variety of shapes and sizes. A further example is that other materials can be used than what is described above.

As to the X-ray sensing member, other types, shapes and dimensions are in principle possible to use. Further, the electric connections to the sensing member and the support of the sensing member may be arranged in other ways. For instance, the contacting of the first and second conductors to the electrodes may be arranged with gold wires instead of using substrates etc., and, if substrates are used, the contacting between the electrodes and the conducting tracks of the substrate may be arranged by other means than an anisotropic conductive compound, such as a conventional conductive adhesive or a small amount of a metal that is placed and melted at the contact points. However, the exemplified use of substrate+anisotropic conductive compound is believed to reduce the angular dependency to a minimum. Two or more sensing members may be arranged inside the energy filter 2 in a stacked manner; each sensing member may be provided with a corresponding substrate or a double-sided substrate (with conductive tracks on both sides) can be arranged between the sensing members.

The flat inner attenuation members 6, 7 are not necessary but may be useful for further improving the detection device.

The invention claimed is:

1. X-ray detection device, comprising:
an X-ray sensing member, and
an X-ray energy filter comprising an attenuation member configured to attenuate low-energy X-rays to a greater extent than high-energy X-rays in a beam or field of X-radiation directed towards the X-ray sensing member, wherein:
the attenuation member is arranged to extend in a spatial manner at least partly around the X-ray sensing member so as to subtend at least a working solid angle in relation to the X-ray sensing member,
the attenuation member, at least over a working area corresponding to the working solid angle, is provided with a plurality of low-attenuation zones distributed over the working area of the attenuation member, wherein the low-attenuation zones are configured to attenuate X-rays only to a small or negligible extent so as to allow passage of both low-energy and high-energy X-rays to a substantially similar extent through the attenuation member towards the X-ray sensing member,
the low-attenuation zones are distributed in relation to the X-ray sensing member in such a way that, when the X-ray detection device is exposed to a beam or field of parallel X-radiation that is directed towards the X-ray sensing member within the working solid angle and that has a width that covers a projected area of the energy filter, only a first portion of a total surface of the X-ray sensing member facing the beam or field of X-radiation is directly exposed to low-attenuated X-rays that pass through the low-attenuation zones, whereas a second remaining portion of the total surface of the X-ray sensing member facing the beam or field of X-radiation is directly exposed only to X-rays that pass through the attenuation member, and
the relation between i) the first portion of the total surface of the X-ray sensing member facing the beam or field of X-radiation and ii) said total surface of the X-ray sensing member facing the beam or field of X-radiation, is substantially constant irrespective of a spatial angle of incidence of the beam or field of X-radiation that falls within the working solid angle.

2. X-ray detection device according to claim 1, wherein the working solid angle is at least 10°, or at least 20°, or at least 45°, or at least 90° (quarter of a sphere), or at least 180° (hemisphere), or at least 270°, or 360° (entire sphere).

3. X-ray detection device according to claim 1, wherein the first portion constitutes 5-80% of the total surface of the X-ray sensing member facing the beam or field of X-radiation, preferably this relation is 10-50%, preferably 15-35%, more preferably 20-30%, and more preferably around 25%.

4. X-ray detection device according to claim 1, wherein:
the attenuation member comprises one or several elements having an atomic number (Z) of at least 23, and
the one or several elements constitutes at least 50% of the weight of the attenuation member, at least within the working solid angle.

5. X-ray detection device according to claim 4, wherein the attenuation member is made of stainless steel.

6. X-ray detection device according to claim 1, wherein:
the attenuation member has a convex side and a concave side, and
the concave side is directed towards the X-ray sensing member.

7. X-ray detection device according to claim 1, wherein the attenuation member, at least within the working solid angle, has a thickness in the range 0.3-3 mm, preferably 0.5-2 mm.

8. X-ray detection device according to claim 1, wherein the low-attenuation zones exhibit a lower area-specific density than the attenuation member.

9. X-ray detection device according to claim 1, wherein:
the low-attenuation zones form isolated zones, and
the attenuation member extends over an area between the low-attenuation zones.

10. X-ray detection device according to claim 1, wherein the low-attenuation zones form through-holes in the attenuation member.

11. X-ray detection device according to claim 1, wherein:
the X-ray sensing member is arranged onto a supporting arrangement comprising an outer support element, and
the outer support element and the attenuation member are configured to fit together and be connected to each other so as to define a working position for the X-ray sensing member in relation to the attenuation member.

12. X-ray detection device according to claim 11, wherein:
the outer support element, when connected to the attenuation member, forms part of the attenuation member, and
the low-attenuation zones are distributed also over the outer support element.

13. X-ray detection device according to claim 11, wherein the supporting arrangement comprises an inner support element that extends between the outer support element and the X-ray sensing member.

14. X-ray detection device according to claim 13, wherein the inner support element is made of a material that exhibits a low or negligible attenuating effect on X-rays, such as a plastic material.

15. X-ray detection device according to claim 13, wherein:
the inner support element and the outer support element forms one integral component, and
the inner support element has a physical structure adapted to exhibit a low or negligible attenuating effect on X-rays directed towards the sensing member.

16. X-ray detection device according to claim 11, wherein:
the device comprises first and second electric connectors connected to the X-ray sensing member,
the outer support element is provided with at least one through-hole, and
the first and second electric connectors extend through the at least one through-hole in the outer support element.

17. X-ray detection device according to claim 1, wherein the X-ray sensing member has a flat shape with first and second main surfaces facing in opposite directions and a perimeter edge.

18. X-ray detection device according to claim 17, wherein:
the attenuation member is arranged to subtend the working solid angle in relation to the edge of the X-ray sensing member, and
the working solid angle in relation to the edge is at least 10°, or at least 20°, or at least 45°, or at least 90°, or at least 180° (hemisphere), or at least 270°, or 360° (entire sphere).

19. X-ray detection device according to claim 17, wherein:
the X-ray sensing member is a semiconducting sensing member provided with first and second electrodes arranged at one of the main surfaces of the X-ray sensing member or one electrode at each main surface of the X-ray sensing member,
the device comprises first and second electric conductors connected to the first and second electrodes, respectively,
the device comprises a non-conducting substrate provided with at least a first conducting track that forms the first electric conductor, and
the connection between the first conducting track and the first electrode is arranged by means of an anisotropic conducting compound.

20. X-ray detection device according to claim 19, wherein the non-conducting substrate is arranged at the surface of the X-ray sensing member and extends substantially in parallel with said surface.

21. X-ray detection device according to claim 19, wherein:
the substrate has a first side facing the X-ray sensing member and a second, opposite side facing away from the X-ray sensing member, and
the first conducting track is arranged on the first side of the substrate.

22. X-ray detection device according to claim 19, wherein the X-ray sensing member is provided with at least one electrode contact point substantially free from surface oxides.

23. X-ray detection device according to claim 22, wherein the anisotropic conductive compound is positioned locally at the at least one electrode contact point.

24. X-ray detection device according to claim 22, wherein:
the X-ray sensing member is provided with a plurality of spaced-apart electrode contact points, and
the anisotropic conductive compound is positioned locally at each of said plurality of spaced-apart electrode contact points so as to form isolated contact point regions containing the compound and to form a space substantially free from the compound between the contact point regions.

25. X-ray detection device according to claim 24, wherein the X-ray sensing member is provided with at least three electrode contact points that are laterally distributed over the surface of the X-ray sensing member in a pattern that defines support positions adapted to the size and shape of the non-conducting substrate so as to, when the anisotropic conductive compound is positioned locally at each of said at least three electrode contact points, provide a support for the non-conducting substrate.

26. X-ray detection device according to claim 25, wherein:
the surface of the X-ray sensing member has a substantially rectangular shape, and
the plurality of electrode contact points comprises four corner contact points arranged at each corner of the rectangular surface and one central contact point arranged in a central region of the rectangular surface.

27. X-ray detection device according to claim 19, wherein the first and second electric conductors are connected to electronic equipment configured for handling of an output signal from the X-ray sensing member, such as an electrometer.

28. X-ray detection device according to claim 19, wherein the non-conducting substrate is made of a plastic or ceramic material, preferably a flexible plastic material.

29. X-ray detection device according to claim 19, wherein the non-conducting substrate has a thickness in the range 25-200 μm.

30. X-ray detection device according to claim 19, wherein the device comprises a substrate supporting member comprising a flat surface arranged at a side of the non-conducting substrate that faces away from the X-ray sensing member.

31. X-ray detection device according to claim 19, wherein the first conducting track is raised, preferably in the range 5-50 μm, in relation to a surrounding substrate surface.

32. X-ray detection device according to claim 19, wherein the first conducting track is made of copper or aluminum.

33. X-ray detection device according to claim 19, wherein:
the anisotropic conductive compound comprises conductive particles distributed in a non-conducting resin or matrix material, and
the compound is non-conducting unless the conductive particles are brought together.

34. X-ray detection device according to claim 33, wherein the anisotropic conductive compound comprises a thermosetting resin.

35. X-ray detection device according to claim 17, wherein:
the first and second electrodes are arranged on the same main surface of the X-ray sensing member,
the substrate is provided with a second conducting track that forms the second electric conductor, and
the connection between the second conducting track and the second electrode is arranged by means of an anisotropic conducting compound.

36. X-ray detection device according to claim 17, wherein:
the first and second electrodes are arranged on opposite main surfaces of the X-ray sensing member,
the device comprises a further non-conducting substrate provided with a further conducting track,
the further substrate is arranged at the second main surface of the X-ray sensing member and extends substantially in parallel with said second main surface, and
the further conducting track forms the second electric conductor.

37. X-ray detection device according to claim 17, wherein each main side of the X-ray sensing member is provided with a flat inner attenuation member that extends alongside of the main side.

* * * * *